United States Patent
Regnier et al.

[11] 3,970,663
[45] July 20, 1976

[54] CERTAIN AMINO-NICOTINAMIDE DERIVATIVES

[75] Inventors: Gilbert Regnier, Chatenay Malabry; Roger Canevari, Villebon-sur-Yvette; Xavier Pascaud, Paris, all of France

[73] Assignee: Science Union et Cie, Societe Francaise de Recherche Medical, Suresnes, France

[22] Filed: Sept. 22, 1975

[21] Appl. No.: 615,452

Related U.S. Application Data

[62] Division of Ser. No. 465,931, May 1, 1974.

[30] Foreign Application Priority Data
May 2, 1973  United Kingdom............... 20842/73

[52] U.S. Cl................ 260/295.5 A; 260/256.4 N;
260/295.5 B; 260/247.2 A; 260/293.69;
424/266; 424/248; 424/267
[51] Int. Cl.².................................... C07D 213/56
[58] Field of Search................ 260/295.5 A, 293.69

[56] References Cited
UNITED STATES PATENTS
3,105,072  9/1963  Felder et al.................. 260/295.5 A
3,108,113  10/1963  Halpern....................... 260/295.5 A

*Primary Examiner*—Alan L. Rotman
*Attorney, Agent, or Firm*—Behr & Woodbridge

[57] ABSTRACT

Heterocyclic amides of the formula:

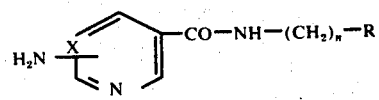

wherein:
X is N or CH;
n is 0 or 1 and
R is

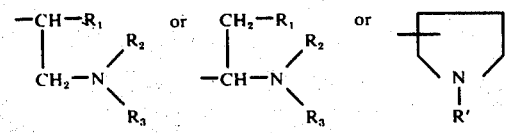

wherein:
$R_1$ is hydrogen or methyl,
$R_2$ and $R_3$ which are the same, are lower alkyl or joined together, represent a polymethylenic chain from $C_4$ to $C_7$ optionally including an oxygen atom, and
R' is saturated or unsaturated acyclic hydrocarbon radicals from $C_1$ to $C_{20}$, cycloalkyl from $C_3$ to $C_7$, Ar - A - or

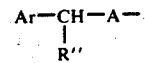

wherein:
A is a single bond or a saturated or unsaturated acyclic hydrocarbon chain from $C_1$ to $C_6$ optionally including an oxygen atom, and
Ar and R'' are aromatic, alkoxy aromatic, methylenedioxy aromatic or polymethylenedioxy aromatic.

These compounds are used as medicine, especially in the treatment of gastric hypersecretion, gastroduodenal ulcers and central nervous system disorders.

7 Claims, No Drawings

CERTAIN AMINO-NICOTINAMIDE DERIVATIVES

This is a division of application Ser. No. 465,931, filed May 1, 1974.

The present invention provides heterocyclic amides of the general formula I :

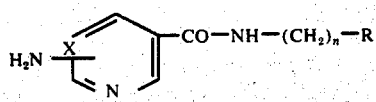

and acid addition salts, especially physiologically tolerable acid addition salts thereof, wherein :

X is selected from the group consisting of N and CH ;

n is selected from 0 and 1, and

R is selected from the group consisting of

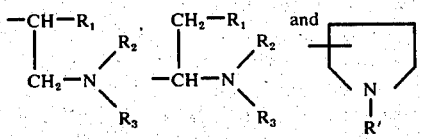

wherein :

$R_1$ is selected from the group consisting of a hydrogen atom and a methyl radical ;

$R_2$ and $R_3$, which are the same, are selected from the group consisting of alkyl radicals having from 1 to 6 carbon atoms inclusive in a linear or branched chain, or $R_2$ and $R_3$ joined together, represent a polymethylenic chain of the formula — $(CH_2)_p$— wherein p is an integer from 4 to 7 inclusive optionally including in the chain an oxygen atom, and R' is selected from the group consisting of saturated and unsaturated acyclic hydrocarbon radicals having from 1 to 20 carbon atoms inclusive in linear and branched chain, a cycloalkyl radical having from 3 to 7 carbon atoms, and radicals of the formula

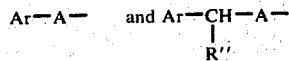

wherein :

A is selected from the group consisting of a single bond and saturated and unsaturated acyclic hydrocarbon radicals having from 1 to 6 carbon atoms inclusive in a linear or branched chain, optionally including in the chain an oxygen atom ; and Ar and R'', which are the same or different, are selected from the group consisting of unsubstituted aromatic radicals and aromatic radicals substituted by one or more radicals selected from the group consisting of linear and branched alkoxy radicals having from 1 to 6 carbon atoms inclusive, methylenedioxy, ethylenedioxy and trimethylenedioxy radicals.

Due to their pharmacological properties, the preferred compounds are :

in one hand, the compounds of the general formula I'

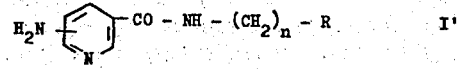

wherein :

n has the meaning given above, and

R is selected from the group consisting of :

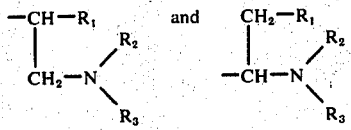

wherein :

$R_1$ has the meaning given above, and $R_2$ and $R_3$ which are the same, are selected from the group consisting of linear and branched alkyl radicals having from 1 to 6 carbon atoms inclusive, and physiologically tolerable acid addition salts thereof, and on the other hand, the compounds of the general formula I'' :

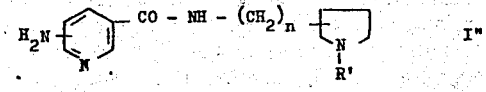

wherein :

n has the meaning given above, and

R' is selected from the group consisting of linear and branched saturated and unsaturated acyclic hydrocarbon radicals having from 1 to 6 carbon atoms inclusive, a cyclohexyl radical, a phenylalkyl radical wherein the alkyl moiety which is linear or branched has from 1 to 6 carbon atoms inclusive or a phenyloxyethyl radical, and physiologically tolerable acid addition salts thereof.

The compounds of the general formula I are new and they were prepared according to the following processes which are included in the present invention.

The present invention provides a process for preparing a compound of the general formula I which comprises reacting a compound of the general formula II :

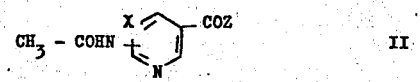

wherein X has the meanings given above and Z represents a chlorine or bromine atom or a - O - COOY radical wherein Y represents an alkyl radical having from 1 to 4 carbon atoms, with a compound of the general formula III :

wherein n and R have the meanings given for the general formula I, and then deacetylating the so-obtained amide of the general formula IV :

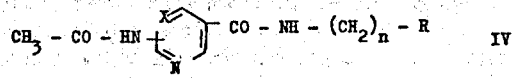

wherein X, n and R have the meanings given for the general formula I, by heating for a short time, at a temperature ≤ 80° C, in the presence of an aqueous alcoholic solution of sodium or potassium hydroxide.

In the case where the first step of the reaction is performed with a compound of the general formula II wherein Z is a chlorine or a bromine atom, which is generally in the form of an addition compound with a hydrogen halide, it is advantageous to operate in a polar solvent, for example an aliphatic amide, for example dimethylformamide or dimethylacetamide, at a temperature within the range of from 50° to 100°C in the presence of an acceptor of the hydrogen halide formed in the course of the reaction. The acceptor may, for example, be a tertiary organic base, for example triethylamine or pyridine, or an excess of the amine of the general formula III.

In the case where the first step of the reaction is performed with a mixed anhydride of the general formula II wherein Z is a —O—COOY radical, the latter may be prepared "in situ" starting from the corresponding acid of the formula II wherein Z is an OH radical and an alkyl chloroformate, for example ethyl chloroformate. It is advantageous to carry out the reaction at a low temperature within the range of from −10 to −5°C in a polar solvent, for example a tertiary amide, for example dimethylformamide, in the presence of an excess of the amine of the general formula III.

The present invention also provides a process for preparing a compound of the general formula I which comprises reacting a compound of the general formula V:

wherein X has the meanings given for the general formula I, with a compound of the general formula VI:

wherein n and R have the meanings given for the general formula I.

The use of such a process is preferable in the case where the deacetylation of a compound of the formula IV is rendered difficult in view of the concomitant hydrolysis of the —CO—NH— bond.

An analogous method was described by GREENSTEIN and WINITZ in "Chemistry of Aminoacids" (1961) 999, especially for preparing polypeptides and consists in activating the amine (III), in the form of a phosphazo derivative thereof, rather than in activating the acid (V).

Such a process is advantageously carried out by reacting the compound of the general formula III with phosphorus trichloride, in stoichiometric proportions, in a solvent such as, for example, pyridine, at a temperature ≤ + 5°C and then condensing the phosphazenic derivative of the general formula VI, so obtained, in situ with an acid of the general formula V, at a temperature within the range of from 80° to 100°C.

The compounds of the general formula I are bases which may be converted with acids into acid addition salts. As acids used for the formation of these addition salts, there may be mentioned, for example, in the mineral series : hydrochloric, hydrobromic, sulfuric and phosphoric acids, and in the organic series : acetic; propionic, maleic, fumaric, tartaric, citric, oxalic, benzoic, methanesulfonic and isethionic acids.

The compounds of the formula I may be purified by physical methods, for example crystallization or chromatography or by chemical methods, for example formation of acid addition salts thereof, crystallization of the latter and decomposition thereof by means of alkaline agents.

The compounds of the general formula I and physiologically tolerable salts thereof possess valuable pharmacological and therapeutic properties, especially gastric antisecretory, antiulcerous, gastro-intestinal motility and central nervous system acting properties.

Their toxicity is low and their $LD_{50}$ determined in mice varies from 114 to more than 2000 mg/kg per os.

The activity of the new compounds on the gastric secretion was demonstrated by the method of H. G. Shay et al. (Gastroent. 5 43, 1945). Regarding the gastric antisecretory activity, the average effective dose ($ED_{50}$) varies from 12.8 to 120 mg/kg when the compounds are administered in the rats by intraduodenal route.

The compounds of the invention also exhibit a very important protecting activity against restraint ulcers. Doses of from 7.27 to 120 mg/kg administered in the rats by an oral route give a 50 % protection compared with untreated control animals. They also possess a protecting activity against ulcers provoked by Aspirin.

Moreover, it was demonstrated by the method of test-meal in the rats (A. F. Green, Brit. J. Pharm. 14, 27, 1959) that the new compounds exert a notable activity on the gastro-intestinal motricity. They also possess an activity on the central nervous system. On the other hand, they have no anticholinergic activity as it was demonstrated by the results of the test of chromodacryorrhea in the rats according to the M. M. Winbury et al.'s method (J. Pharmacol. Exp. Therap. 95, 53, 1949).

The low toxicity and the above-described pharmacological properties enable the compounds of the invention to be used in therapy and especially in the treatment of gastric hypersecretion, gastroduodenal ulcers, and central nervous system disorders. The present invention also provides a pharmaceutical preparation which contains a compound of the general formula I or a physiologically tolerable salt thereof in admixture or conjunction with a pharmaceutically suitable carrier. As pharmaceutical suitable carriers, there may be mentioned for example, distilled water, starch, talc, glucose, lactose, ethylcellulose, magnesium stearate or cocoa butter.

The so-obtained pharmaceutical preparations are advantageously in unit dosage form and may contain from 20 to 500 mg of the active ingredient.

These pharmaceutical preparations may be in form of tablets, dragees, capsules, suppositories or injectable or drinkable solutions and may be administered by oral, rectal or parenteral route at a dose of from 20 to 500 mg in active ingredient.

The following examples illustrate the invention, the melting points being determined in a capillary tube unless otherwise stated.

EXAMPLE 1

2-(6-amino nicotinamidomethyl)-1-ethyl pyrrolidine

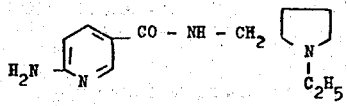

A solution of 14.4 g of ethyl chloroformate in 20 ml of anhydrous dimethyl formamide was added, over a period of 15 minutes at a temperature of −10°C, to a solution of 12 g of 6-acetamido nicotinic acid and 13.4 g of triethylamine in 250 ml of anhydrous dimethylformamide. The mixture was allowed to stand for two hours at −10°C and then a solution of 17.1 g of 2-amino-methyl-1-ethyl pyrrolidine in 150 ml of dimethylformamide was added.

The reaction mixture was allowed to stand for 17 hours at a room temperature and then the so-formed triethylamine hydrochloride was suction-filtered off. The dimethylformamide was evaporated off under reduced pressure and then the residue was triturated with 400 ml of ether. The semi-crystalline residue was dissolved in 150 ml of a 2 N methanesulphonic acid solution. The solution was filtered and was then alkalinized with an excess of $K_2CO_3$. The so-obtained crystalline product was suction-filtered off and there were obtained 12.8 g of 2-(6-acetamido nicotinamidomethyl)-1-ethyl pyrrolidine, in the form of beige crystals melting (Kofler) at 163°C. The latter was deacetylated by heating under reflux for 15 minutes in the presence of 4.8 g of potassium hydroxide, 140 ml of ethanol and 6 ml of water. There were finally obtained 6.8 g of 2-(6-amino nicotinamidomethyl)-1-ethyl pyrrolidine, in the form of beige crystals melting (Kofler) at 136°C. 2-(6-amino nicotinamidomethyl)-1-ethyl pyrrolidine was also prepared as follows :

A mixture of 12.8 g (0.1 mole) of 2-aminomethyl-1-ethyl pyrrolidine and 22.2 g (0.11 mole) of triethylamine was added at a temperature 20°C, to a solution of 23.5 g (0.1 mole) of 3-chlorocarbonyl-6-acetamido pyridine hydrochloride (itself prepared starting from 6-acetamido nicotinic acid) in 250 ml of anhydrous dimethylformamide. After the completion of the addition, the mixture was heated to 50°C for 1 hour then dimethylformamide was eliminated under reduced pressure. The oily residue was triturated with 200 ml of water and 100 ml of ether. The so-obtained base crystallized and there were obtained 17.4 g of 2-(6-acetamido nicotinamidomethyl)-1-ethyl pyrrolidine in the form of beige crystals melting (Kofler) at 162°–163°C. This compound was deacetylated according to the above described method and there were finally obtained 9.8 g of 2-(6-amino nicotinamidomethyl)-1-ethyl pyrrolidine, melting (Kofler) at 136°C.

EXAMPLES 2 to 24

The following compounds were prepared according to the methods described in Example 1.

2. 2-(2-amino nicotinamidomethyl)-1-ethyl pyrrolidine, M.P. of its dihydrochloride : 235°–238°C (ethanol), starting from 2-acetamido nicotinic acid and 2-aminomethyl-1-ethyl pyrrolidine.

3. 2-(2-amino-5-pyrimidinyl carboxamidomethyl)-1-ethyl pyrrolidine, M.P. 179°–183°C (ethyl acetate), starting from 2-acetamido-5-pyrimidinyl carboxylic acid and 2-aminomethyl-1-ethyl pyrrolidine 4. 3-(6-amino nicotinamidomethyl)-1-ethyl pyrrolidine, M.P. 138°–140°C (ethyl acetate), starting from 6-acetamido nicotinic acid and 3-aminomethyl-1-ethyl pyrrolidine.

5. 2-(6-amino nicotinamidomethyl)-1-butyl pyrrolidine, M.P. 64°–67°C (ether), starting from 6-acetamido nicotinic acid and 2-aminomethyl-1-butyl pyrrolidine.

6. 2-(6-amino nicotinamidomethyl)-1-allyl pyrrolidine, M.P. 106°–107°C (ethyl acetate), starting from 6-acetamido nicotinic acid and 2-aminomethyl-1-allyl pyrrolidine.

7. 2-(6-amino nicotinamidomethyl)-1-phenylethyl pyrrolidine, M.P. of its hemihydrate 93°–96°C (ethyl acetate), starting from 6-acetamido nicotinic acid and 2-aminomethyl-1-phenylethyl pyrrolidine.

8. 2-(6-amino nicotinamidomethyl)-1-piperonyl pyrrolidine, M.P. of its difumarate 197°–199°C (ethanol), starting from 6-acetamido nicotinic acid and 2-aminomethyl-1-piperonyl pyrrolidine.

9. 2-(6-amino nicotinamidomethyl)-1-cyclohexyl pyrrolidine, M.P. 150°–152°C (ethyl acetate), starting from 6-acetamido nicotinic acid and 2-aminomethyl-1-cyclohexyl pyrrolidine.

10. 2-(6-amino nicotinamidomethyl)-1-phenyl pyrrolidine, M.P. 217°–219°C (methanol), starting from 6-acetamido nicotinic acid and 2-aminomethyl-1-phenyl pyrrolidine.

11. 5-diethylaminoethylcarbamoyl-2-amino pyridine, M.P. of its dihydrochloride hemihydrate 137°–139°C (isopropanol at 98 %), starting from 2-acetamido-5-pyridyl carboxylic acid and diethylaminoethylamine.

12. 5-(2-diethylaminopropylcarbamoyl)-2-amino pyridine, M.P. 141°–145°C, starting from 2-acetamido-5-pyridyl carboxylic acid, and 2-diethylaminopropylamine.

13. 5-(3-diethylamino-2-propyl carbamoyl)-2-amino pyridine, M.P. of its difumarate 178°–180°C (anhydrous methanol), starting from 2-acetamido-5-pyridyl carboxylic acid and 3-diethylamino-2-propylamine.

14. 3-(6-amino nicotinamido)-1-ethyl pyrrolidine, M.P. 218°–219°C (dioxane), starting from 6-acetamido nicotinic acid and 3-amino-1-ethyl pyrrolidine.

15. 2-(6-amino nicotinamidomethyl)-1-cyclopropyl pyrrolidine, M.P. 149°–150°C starting from 6-acetamido nicotinic acid and 2-aminomethyl-1-cyclopropyl pyrrolidine.

16. 2-(6-amino nicotinamidomethyl)-1-isopropyl pyrrolidine, M.P. 152°–154°C (ethyl acetate), starting from 6-acetamido nicotinic acid and 2-aminomethyl-1-isopropyl pyrrolidine.

17. 2-(6-amino nicotinamidomethyl)-1-isobutyl pyrrolidine, M.P. 151°–152°C (ethyl acetate), starting from 6-acetamido nicotinic acid and 2-aminomethyl-1-isobutyl pyrrolidine.

18. 2-(6-amino nicotinamidomethyl)-1-cinnamyl pyrrolidine, M.P. 110°–112°C, starting from 6-acetamido nicotinic acid, and 2-aminomethyl-1-cinnamyl pyrrolidine.

19. 2-(6-amino nicotinamidomethyl)-1-(3-phenylpropyl) pyrrolidine, M.P. 93°–96°C (ethyl acetate), starting from 6-acetamido nicotinic acid and 2-aminomethyl-1-(3-phenyl propyl) pyrrolidine.

20. 2-(6-amino nicotinamidomethyl)-1-(3-phenyl-2-propyl) pyrrolidine, M.P. of its difumarate 181°–182°C (methanol), starting from 6-acetamido nicotinic acid and 2-aminomethyl-1-(3-phenyl-2-propyl) pyrrolidine.

21. 2-(6-amino nicotinamidomethyl)-1-(3,3-diphenylpropyl) pyrrolidine, M.P. of its difumarate 179°–181°C, starting from 6-acetamido nicotinic acid and 2-aminomethyl-1-(3,3-diphenyl propyl) pyrrolidine.

22. 2-(6-amino nicotinamidomethyl)-1-phenoxy ethyl pyrrolidine, M.P. of its dihydrochloride 194°–196°C (ethanol), starting from 6-acetamido nicotinic acid and 2-aminomethyl-1-phenoxyethyl pyrrolidine.

23. 5-(2-morpholinopropyl carbamoyl)-2-amino pyridine, M.P. 162°–163°C (ethyl acetate), starting from 2-acetamido-5-pyridyl carboxylic acid and 2-morpholino propylamine.

24. 5-(2-piperidinopropyl carbamoyl)-2-amino pyridine, M.P. 161°–163°C (ethyl acetate), starting from 2-acetamido-5-pyridyl carboxylic acid and 2-piperidino propylamine.

EXAMPLE 25

2-(2-amino nicotinamidomethyl)-1-ethyl pyrrolidine

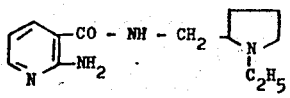

A solution of 14 g of phosphorus trichloride in 8 ml of pyridine was added, over a period of two hours at a temperature of −5°C, to a solution of 26.4 g of 2-aminomethyl-1-ethyl pyrrolidine in 40 ml of pyridine.

The mixture was allowed to stand at a room temperature for one and a half hours and then 13.8 g of 2-amino nicotinic acid were added. The mixture was heated at 95°–100°C for 3 hours and was then allowed to stand at a room temperature for 24 hours. The semicrystalline mixture was alkalinized with 150 ml of a 2 N sodium hydroxide solution and was then extracted several times with CHCl$_3$.

The chloroformic solution was washed with water, the solvent was distilled off under reduced pressure and the residue was taken up with 300 ml of petroleum ether. The crystallized product was suction-filtered off. There were obtained 9 g of 2-(2-amino nicotinamidomethyl)-1-ethyl pyrrolidine which when treated with HCl in ethanol, gave 7 g of 2-(2-amino nicotinamidomethyl)-1-ethyl pyrrolidine, dihydrochloride in the form of white crystals melting at 235°–238°C.

EXAMPLES 26 to 48

The following compounds were prepared according to the process described in Example 25 :

26. 2-(6-amino nicotinamidomethyl)-1-ethyl pyrrolidine, M.P. (Kofler) : 136°C, starting from P Cl$_3$, 2-aminomethyl-1-ethyl pyrrolidine and 6-amino nicotinic acid.

27. 2-(2-amino-5-pyrimidinyl carboxamidomethyl)-1-ethyl pyrrolidine, M.P. 179°–183°C (ethyl acetate), starting from P Cl$_3$, 2-aminomethyl-1-ethyl pyrrolidine and 2-amino-5-pyrimidinyl carboxylic acid.

28. 3-(6-amino nicotinamidomethyl)-1-ethyl pyrrolidine, M.P. 138°–140°C (ethyl acetate), starting from P Cl$_3$, 3-aminomethyl-1-ethyl pyrrolidine and 6-amino nicotinic acid.

29. 2-(6-amino nicotinamidomethyl)-1-butyl pyrrolidine, M.P. 64°–67°C (ether), starting from P Cl$_3$, 2-aminomethyl-1-butyl pyrrolidine and 6-amino nicotinic acid.

30. 2-(6-amino nicotinamidomethyl)-1-allyl pyrrolidine, M.P. 106°–107°C (ethyl acetate), starting from P Cl$_3$, 2-aminomethyl-1-allyl pyrrolidine and 6-amino nicotinic acid.

31. 2-(6-amino nicotinamidomethyl)-1-phenylethyl pyrrolidine, M.P. of its hemihydrate 93°–96°C (ethyl acetate), starting from P Cl$_3$, 2-aminomethyl-1-phenylethyl pyrrolidine and 6-amino nicotinic acid.

32. 2-(6-amino nicotinamidomethyl)-1-piperonyl pyrrolidine, M.P. of its difumarate : 197°–199°C (ethanol), starting from P Cl$_3$, 2-aminomethyl-1-piperonyl pyrrolidine and 6-amino nicotinic acid.

33. 2-(6-amino nicotinamidomethyl)-1-cyclohexyl pyrrolidine, M.P. 150°–152°C (ethyl acetate), starting from P Cl$_3$, 2-aminomethyl-1-cyclohexyl pyrrolidine and 6-amino nicotinic acid.

34. 2-(6-amino nicotinamidomethyl)-1-phenyl pyrrolidine, M.P. 217°–219°C (methanol), starting from P Cl$_3$, 2-aminomethyl-1-phenyl pyrrolidine and 6-amino nicotinic acid.

35. 5-diethylaminoethylcarbamoyl-2-amino pyridine, M.P. of its dihydrochloride hemihydrate : 137°–139°C (isopropanol at 98 %), starting from P Cl$_3$, diethylaminoethylamine and 2-amino-5-pyridyl carboxylic acid.

36. 5-(2-diethylaminopropylcarbamoyl)-2-amino pyridine, M.P. 141'–145°C, starting from P Cl$_3$, 2-diethylamino propylamine and 2-amino-5-pyridyl carboxylic acid.

37. 5-(3-diethylamino-2-propyl carbamoyl)-2-amino pyridine, M.P. of its difumarate 178°–180°C (anhydrous methanol), starting from P Cl$_3$, 3-diethylamino-2 propylamine and 2-amino-5-pyridyl carboxylic acid.

38. 3-(6-amino nicotinamido)-1-ethyl pyrrolidine, M.P. 218°–219°C (dioxane), starting from P Cl$_3$, 3-amino-1-ethyl pyrrolidine and 6-amino nicotinic acid.

39. 2-(6-amino nicotinamidomethyl)-1-cyclopropyl pyrrolidine, M.P. 149°–150°C, starting from P Cl$_3$, 2-aminomethyl-1-cyclopropyl pyrrolidine and 6-amino nicotinic acid.

40. 2-(6-amino nicotinamidomethyl)-1-isopropyl pyrrolidine, M.P. 152°–154°C (ethyl acetate), starting from P Cl$_3$, 2-aminomethyl-1-isopropyl pyrrolidine and 6-amino nicotinic acid.

41. 2-(6-amino nicotinamidomethyl)-1-isobutyl pyrrolidine, M.P. 151°–152°C (ethyl acetate), starting from P Cl$_3$, 2-aminomethyl-1-isobutyl and 6-amino nicotinic acid.

42. 2-(6-amino nicotinamidomethyl)-1-cinnamyl pyrrolidine, M.P. 110°–112°C, starting from P Cl$_3$, 2-aminomethyl-1-cinnamyl pyrrolidine and 6-amino nicotinic acid.

43. 2-(6-amino nicotinamidomethyl)-1-(3-phenylpropyl) pyrrolidine, M.P. 93°–96°C (ethyl acetate), starting from P Cl$_3$, 2-aminomethyl-1-(3-phenylpropyl) pyrrolidine and 6-amino nicotinic acid.

44. 2-(6-amino nicotinamidomethyl)-1-(3-phenyl-2-propyl) pyrrolidine, M.P. of its difumarate 181°–182°C (methanol), starting from P Cl$_3$, 2-aminomethyl-1-(3-phenyl-2-propyl) pyrrolidine and 6-amino nicotinic acid.

45. 2-(6-amino nicotinamidomethyl)-1-(3,3-diphenylpropyl) pyrrolidine, M.P. of its difumarate 179°–181°C, starting from P Cl₃, 2-aminomethyl-1-(3,3-diphenylpropyl) pyrrolidine and 6-amino nicotinic acid.

46. 2-(6-amino nicotinamidomethyl)-1-phenoxy ethyl pyrrolidine, M.P. of its dihydrochloride 194°–196°C (ethanol), starting from P Cl₃, 2-aminomethyl-1-phenoxyethyl pyrrolidine and 6-amino nicotinic acid.

47. 5-(2-morpholinopropyl carbamoyl)-2-amino pyridine, M.P. 162°–163°C (ethyl acetate), starting from P Cl₃, 2-morpholinopropylamine and 2-amino-5-pyridyl carboxylic acid.

48. 5-(2-piperidinopropyl carbamoyl)-2-amino pyridine, M.P. 161°–163°C (ethyl acetate), starting from P Cl₃, 2-piperidinopropylamine and 2-amino-5-pyridyl carboxylic acid.

We claim:

1. A compound selected from the group consisting of:

A. Heterocyclic amides of the general formula I:

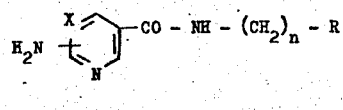

wherein:
X is CH;
n is selected from 0 and 1, and
R is selected from the group consisting of:

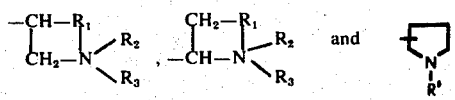

wherein:
R₁ is selected from the group consisting of hydrogen and methyl, R₂ and R₃ joined together represent a polymethylenic chain of the formula —(CH₂)ₚ— wherein p is an integer from 4 to 7 inclusive and
R' is selected from the group consisting of saturated and unsaturated acyclic hydrocarbon radicals having from 1 to 6 carbon atoms inclusive in linear and branched chains, cycloalkyl having from 3 to 7 carbon atoms, and radicals of the formula:

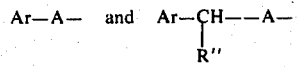

wherein:
A is selected from the group consisting of a single bond and saturated and unsaturated acyclic hydrocarbon radicals having from 1 to 6 carbon atoms inclusive in linear and branched chains, and
Ar and R'', which are the same or different, are selected from the group consisting of unsubstituted phenyl or phenyl substituted by one or more radicals selected from the group consisting of linear and branched alkoxy having from 1 to 6 carbon atoms inclusive, methylenedioxy, ethylenedioxy and trimethylenedioxy; and
B. physiologically tolerable acid addition salts thereof.

2. A compound of claim 1 which is selected from the group consisting of:
A. Heterocyclic amides of the general formula I'':

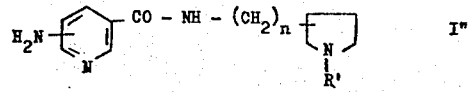

wherein:
n has the meaning given in claim 1, and
R' is selected from the group consisting of linear and branched saturated and unsaturated acyclic hydrocarbon radicals having from 1 to 6 carbon atoms inclusive, cyclohexyl, phenylalkyl wherein the alkyl moiety which is linear or branched has from 1 to 6 carbon atoms inclusive, and phenyloxyethyl; and
B. physiologically tolerable acid addition salts thereof.

3. A compound of claim 1 which is 2-(6-amino nicotinamidomethyl)-1-ethyl pyrrolidine.

4. A compound of claim 1 which is 2-(6-amino nicotinamidomethyl)-1-isobutyl pyrrolidine.

5. A compound of claim 1 which is 2-(6-amino nicotinamidomethyl)-1-allyl pyrrolidine.

6. A compound of claim 1 which is 2-(6-amino nicotinamidomethyl)-1-(3-phenylpropyl) pyrrolidine.

7. A compound of claim 1 which is 2-(6-amino nicotinamidomethyl)-1-(3-phenyl-2-propyl) pyrrolidine.

* * * * *